APPLE TREE

Filed Dec. 26, 1972

United States Patent Office

Plant Pat. 3,556
Patented May 28, 1974

3,556
APPLE TREE

Arlie M. Ward, Wenatchee, Wash., assignor to Van Well Nursery, Inc., Wenatchee, Wash.

Filed Dec. 26, 1972, Ser. No. 318,101
Int. Cl. A01h 5/03
U.S. Cl. Plt.—35 1 Claim

ABSTRACT OF THE DISCLOSURE

A delicious apple tree with fruit that colors earlier and darker red than that of its parent, Brauns, Plant Pat. No. 1,411.

BACKGROUND OF DISCOVERY

This discovery concerns a new and distinct delicious apple tree originating as a whole tree sport or mutation in the orchard of the present applicant in East Wenatchee, Douglas County, Washington, containing trees of the Brauns variety described in U.S. Plant Pat. No. 1,411. While this newly discovered variety most nearly resembles its parent Brauns, it clearly differs therefrom in the earlier appearance of color on the fruit, starting with a very fine stripe, in the darker finishing color (dark blackish-purple blush), and in the smaller and proportionately narrower leaves.

All other characteristics substantially conform to the parent variety.

The new variety has been reproduced through successive generations at Wenatchee, Washington, and in North Carolina by budding and the aforegoing color and leaf characteristics appear stable.

DETAILED DESCRIPTION

Figure 1:
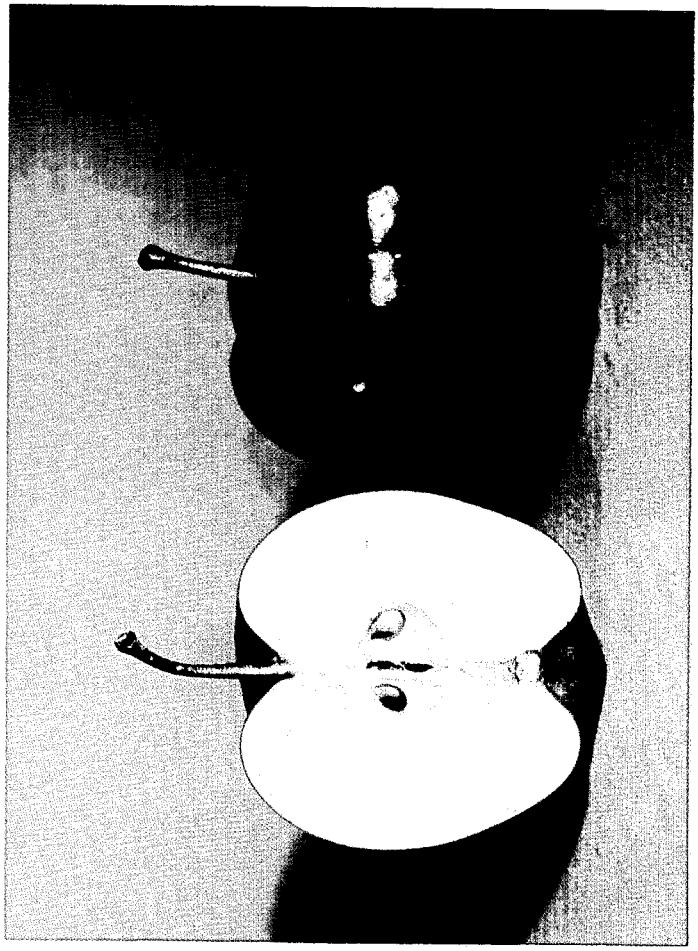
FIG. 1 is a color photograph of the fruit of the new variety.
Figure 2:
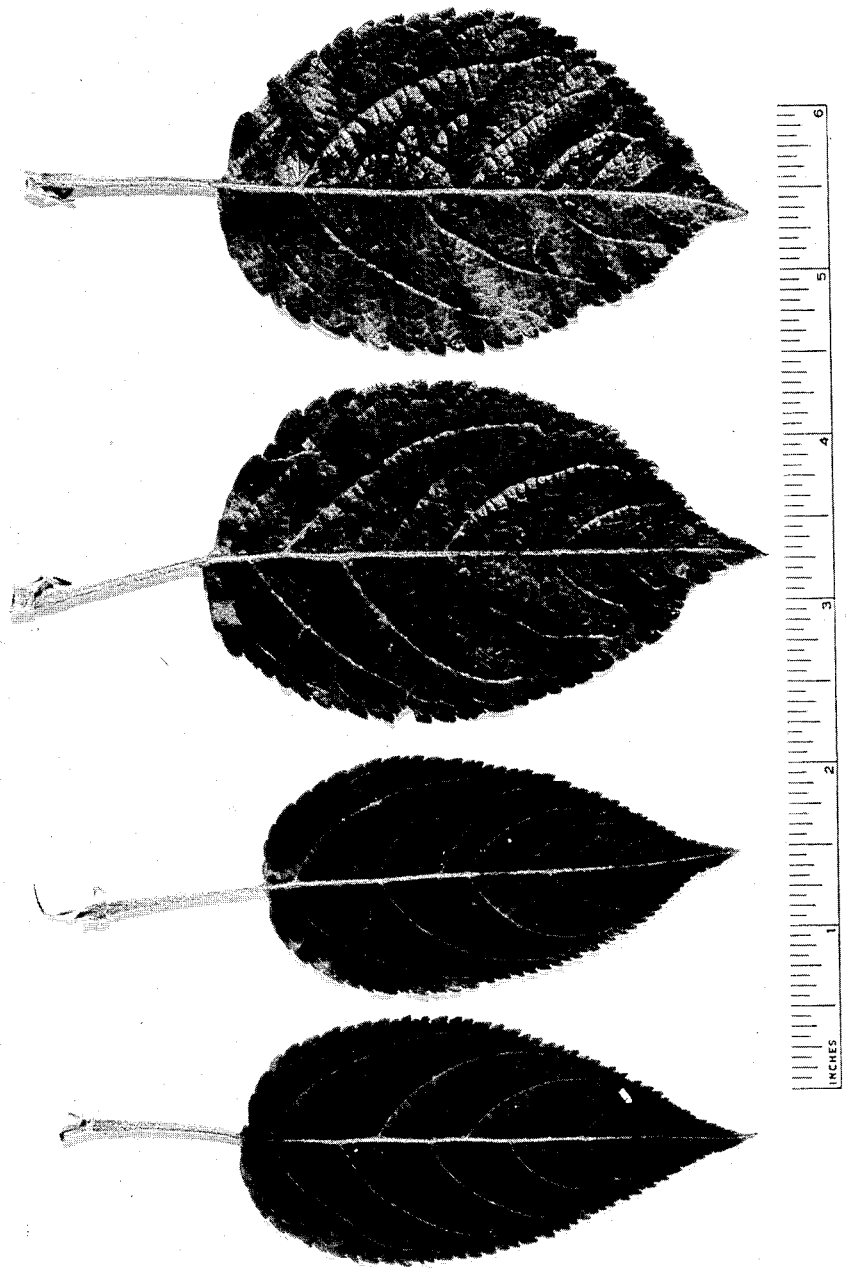
FIG. 2 is a black-and-white photograph of two leaves of the new variety at the left and two leaves of an adjacent parent Brauns tree at the right, all shown from the top side.
Figure 3:
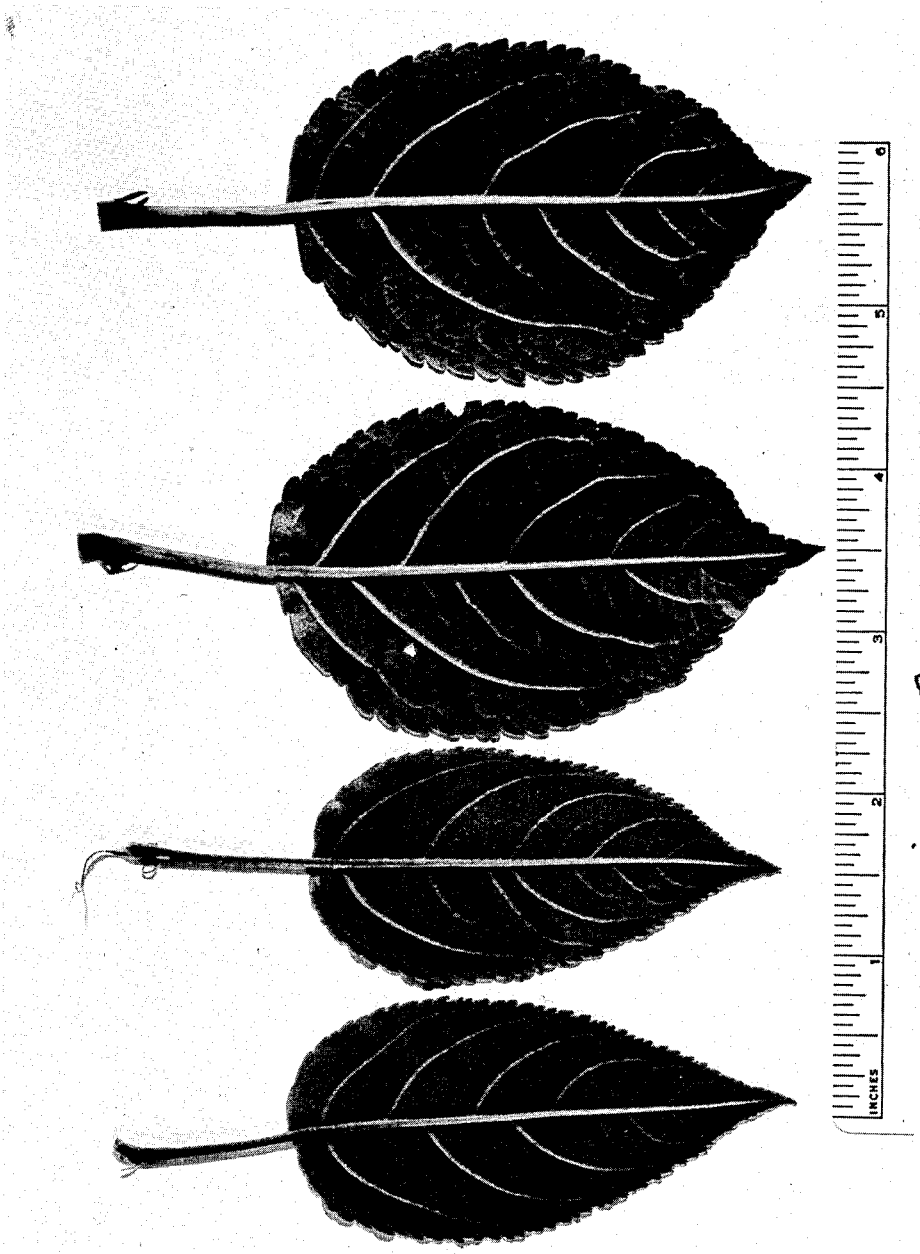
FIG. 3 is a similar photograph showing the same leaves from the underside.

The nearest related variety is Brauns, Plant Pat. No. 1,411. Fruit of the new variety attains fancy red color some four weeks before fruit of the parent. By the time the parent attains fancy red color, the new variety reaches a very dark, even blackish-purple color. The coloration starts with a very fine stripe formation, and the stripes become largely invisible as the depth of color increases. The stems of the apples are red. In Wenatchee the new variety attains extra fancy color by August 1 in an average year.

In color comparisons made over a three-year period (1965, 1966 and 1967) at Wenatchee, the new variety colored approximately fifteen days earlier than the following: "Oregon Red," Plant Pat. No. 2,816; "Topred," Plant Pat. No. 1,916; "Bisbee," Plant Pat. No. 1,565; "Sharp Red," unpatented; and "Wellspur," unpatented.

The following characteristics more fully identify this new variety:

Tree: Medium to large, vigorous, upright, hardy, productive, regular bearer.

Trunk: Smooth.

Branches: Smooth and upright.

Leaves: Small, average length 3" and width 1⅝", medium thickness, underside color of leaf light green, "Ridgeway" Plate XLVII, No. 25, tone b, name Tea Green.

Flower: Similar to parent. Color: White with pink tinge (blooming in Wenatchee area about April 25 to May 5).

Fruit: Maturity similar to parent. Color of fruit blackish-purple, "Ridgeway" Plate XII, No. 67, tone K, name Blackish-Purple.

Stem: Medium length, 1"–1½" at maturity. Color of stem, natural red, "Ridgeway" Plate XXXVII, No. 71VRR, color K.

I claim:

1. The new and distinct variety of apple tree as illustrated and described, characterized by the intensity of dark color of the fruit, the red stem color, the small, narrow leaf, and the early coloration characteristics of its fruit.

No references cited.

ROBERT E. BAGWILL, Primary Examiner